United States Patent [19]

Cribbs et al.

[11] Patent Number: 4,612,809
[45] Date of Patent: Sep. 23, 1986

[54] CURVED-ARRAY ULTRASONIC PROBE USING LOW-VELOCITY FLUID

[75] Inventors: Robert W. Cribbs, Placerville; Claudio I. Zanelli, Fair Oaks, both of Calif.

[73] Assignee: Sound Products Company, L.P., New York, N.Y.

[21] Appl. No.: 550,914

[22] Filed: Nov. 10, 1983

Related U.S. Application Data

[63] Continuation-in-part of Ser. No. 436,182, Oct. 22, 1982, abandoned.

[51] Int. Cl.$^4$ ............................................. G01N 29/00
[52] U.S. Cl. .......................................... 73/626; 73/644; 128/660
[58] Field of Search ................. 73/596, 625, 626, 644; 128/660

[56] References Cited

U.S. PATENT DOCUMENTS

| | | | |
|---|---|---|---|
| 4,059,098 | 11/1977 | Murdock | 73/570 |
| 4,281,550 | 8/1981 | Erikson | 73/626 |
| 4,294,119 | 10/1981 | Soldner | 73/625 |
| 4,389,720 | 6/1983 | Miller | 73/644 |
| 4,391,281 | 7/1983 | Green | 73/644 |
| 4,421,118 | 12/1983 | Dow et al. | 73/620 |

*Primary Examiner*—Howard A. Birmiel
*Attorney, Agent, or Firm*—Weissenberger & Peterson

[57] ABSTRACT

A small, simple, yet accurate probe for producing a sector scan for ultrasonic medical diagnostic apparatus is provided by positioning a curved transducer array within the probe opposite a window, and filling the probe with a fluid having an acoustic velocity on the order of $0.5 \times 10^5$ cm/sec. This combination is made possible by forming the window from a stiff polyionomer material whose acoustic velocity is closed to that of human skin, yet which is stiff enough even when thin to be essentially non-deformable in clinical use. Grating lobes of the ultrasonic beam, as well as the scatter produced within the probe by the high reflectivity of the window material, are absorbed by coating or lining the inner side walls of the probe with an open-celled polyether urethane foam having a cell diameter slightly smaller than one wavelength of the ultrasound in the probe fluid.

9 Claims, 4 Drawing Figures

CURVED-ARRAY ULTRASONIC PROBE USING LOW-VELOCITY FLUID

RELATED CASE INFORMATION

This application is a continuation-in-part of my co-pending application Ser. No. 436,182 filed Oct. 22, 1982 now abandoned and entitled CURVED ARRAY PROBE FOR ULTRASONIC DIAGNOSTICS.

FIELD OF THE INVENTION

This invention relates to probes for ultrasonic diagnostic apparatus, and more particularly to a curved-array probe using a fluid of low acoustic velocity.

BACKGROUND OF THE INVENTION

In the field of medical diagnostics, real-time observation of body processes detected by ultrasonic scans is conventionally done on television monitors. The echoes received by the ultrasonic probe are translated by a scan converter into luminance signals appropriately positioned on the monitor screen to form an image of the patient's internal organs.

In order to synchronize the ultrasonic scan with the standard television format, it is desirable to provide an array of ultrasonic transducers, successive portions of which are pulsed during the horizontal retrace intervals of the television picture. Because of the fact that some vital organs need to be observed through the rib cage, it is often necessary to produce a sector scan, i.e. a fan-shaped group of ultrasonic beams which is centered between two ribs near the skin surface and subtends an angle of about 90°.

Several methods of achieving this result have been proposed. For example, a linear array of transducers may be placed against the patient's skin, and the beam may be steered in an arc by changing the phase of the elements of the array. Because of the accuracy required for this type of operation phased arrays are very expensive.

In U.S. Pat. No. 4,281,550 Erikson, it has been proposed to accomplish this result by means of a stationary probe containing a curved array of individually switchable transducers disposed along an arc of a circle whose center roughly coincides with an acoustically transparent window at which the probe is applied to the patient's skin.

Accuracy requirements for this type of probe are about an order of magnitude lower, because the scanning is done by mere translation of the beam along the array, while the steering is done by the geometry of the array.

The disadvantage of the curved-array probe is that, inasmuch as the array cannot be directly applied to the patient's skin, an acoustic fluid must be interposed within the probe between the array and the window. The easiest way of minimizing refraction, distortion and artifacts at the fluid-window-skin interface is to use a fluid (e.g. water) which matches as closely as possible the acoustic velocity of the skin. Unfortunately, the need to prevent interface reflection artifacts from appearing in the image dictates that the round-trip propagation time between the array and the window be greater than the round-trip propagation time of the beam between the window and the farthest point in the patient's body to be examined. This causes the probe to be large, heavy, and clumsy to handle. In addition, the beam-spread loss characteristics of water dictate the use of a large active array area requiring large numbers of transducer elements and complex electronics.

It was proposed in U.S. Pat. No. 4,242,912 to Burckhardt that a fluid with a relatively slow sound propagation velocity be used as the coupling fluid in an ultrasonic probe. U.S. Pat. No. 4,391,281 to Green subsequently proposed, in connection with a probe containing a mechanically oscillating transducer, that the probe fluid be a fluorocarbon, specifically Fluorinert FC 75 manufactured by 3M Company. However, these teachings were not directly applicable to curved-array probes because the use of a slow fluid in a curved-array probe causes reflection, refraction, and distortion problems which long defied practical solution.

Specifically, it was found that because of the refraction of the beam at the fluid-window-skin interface (which allows a slow-fluid curved-array probe to be much lighter, smaller, cheaper, and less complex than a water-filled one), the stiffness of the window became critical. For example, with the highly desirable Fluorinert FC 72 as the probe fluid, a movement of as little as 0.15 mm in the window surface causes the focus of the beam to vary between 8 cm and infinity. The only way to prevent such movement when the probe was applied to a patient's skin was to provide a thermally stable window of high structural integrity to maintain its shape. Such a window, however, would have to be made of a thick, hard material which, it was generally believed, would inherently have a very high acoustic velocity. Not only would such a material prevent scanning the beam through 90° in the patient's body (because the slow fluid-hard window interface would, due to Snell's law, cause total reflection at even a low angle of incidence from the vertical), but it would also cause unacceptable multiple reflections and scattering from the probe walls sufficient to degrade the image beyond commercial practicality. For this reason, slow fluid was never in fact used in a commercial curved-array probe.

SUMMARY OF THE INVENTION

The present invention makes practical a slow-fluid, curved-array ultrasonic medical probe by providing a probe whose side walls have highly effective attenuation characteristics to suppress grating lobes and scatter, and which has a thin yet stable window with matching characteristics such as to minimize reverberation and scatter to the point where they produce no visible artifacts in the diagnostic image.

Specifically, the probe of this invention uses a window made of a polyionomer which is hard and stiff and has an acoustic velocity on the order of $1.5 \times 10^5$ cm/sec. In accordance with the invention, the side walls of the probe are lined with an open-celled polyether urethane foam with a median cell diameter slightly less than one wavelength and increasing from its surface toward its base.

It is thus the primary object of this invention to provide a curved-array ultrasonic medical probe using a probe fluid with very slow sound propagation characteristics so as to produce an accurate, artifact-free full sector scan with a small, light probe which can be operated by comparatively simple and inexpensive switching electronics.

It is a further object of the invention to provide a window suitable for the practical use of a flow fluid in a curved-array ultrasonic medical probe.

It is another object of the invention to provide effective absorption grating lobes and scatter in a probe of the type described.

DESCRIPTION OF THE PREFERRED EMBODIMENT

Figure 1:
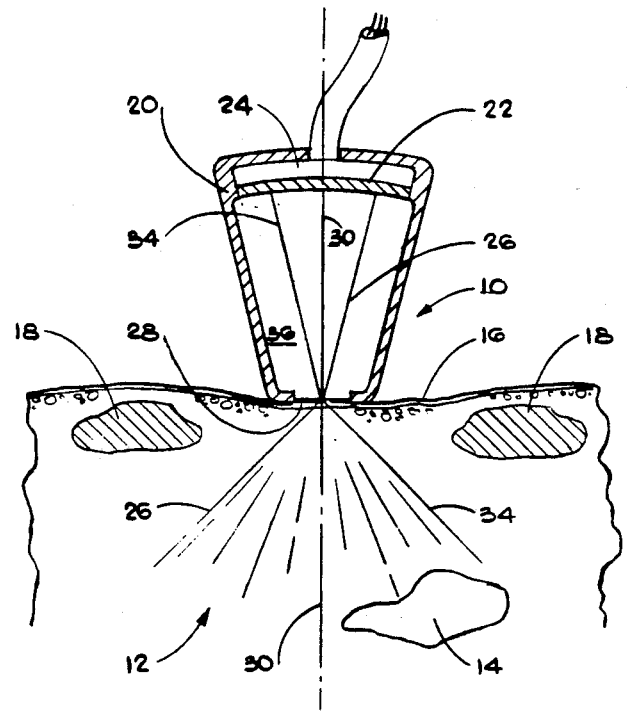
FIG. 1 is a schematic view of the probe of this invention as applied to a human body for diagnostic purposes.

FIG. 1 shows a curved-array ultrasonic probe 10 applied to a human body 12 to produce a sector scan of an organ 14 from a point at the skin surface 16 between two adjacent ribs 18.

The probe 10 is conventionally composed of a housing 20 which contains a large number of transducer elements 21 (FIG. 2) disposed side-by-side in a row to form a curved transducer array 22. An electronic switching matrix 24 of conventional design is incorporated in the probe 10 to activate the transducers of the array 22 in selectable groups. The array 22 in the preferred embodiment of this invention contains about 100 transducer elements. The overall length of the array 22 may be on the order of 5 cm.

The ultrasonic beam is moved along the array 22 in a conventional manner by activating the transducer elements in groups of about thirty-two, with the active group being incrementally shifted from one end of the array 22 to the other in a number of steps dictated by the requirements of the imaging electronics (typically sixty-four). For this type of grouping, the width of each element, in accordance with the invention, is preferably on the order of 0.75 mm to provide optimum resolution within the patient's body. The first step (using, typically, the thirty-two rightmost elements of the array 22) results in a beam 26 which is preferably focused inside the body 12 at a distance of about 10 cm from the window 28 at which the probe 10 is applied to the body 12.

Figure 3:
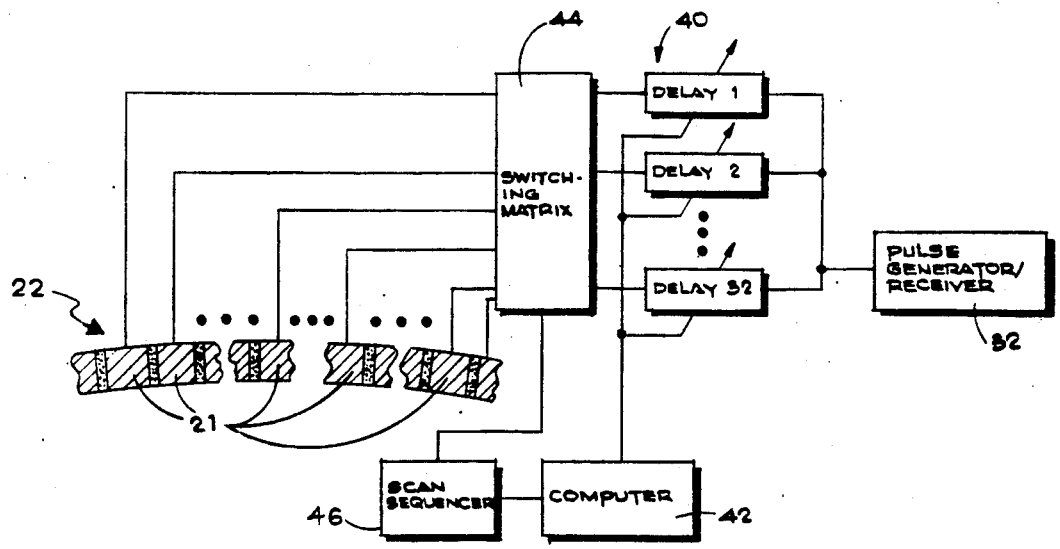
FIG. 3 is a block diagram showing the manner in which the transducers of the curved array are pulsed.

As the active element group of the array 22 is translated toward the left in FIG. 1, ultrasonic beams are transmitted at various angles. When the thirty-two centermost elements are activated, a beam 30 is formed which is transmitted into the body 12 perpendicularly to the window 28. During the interval between pulses, echoes are received by the same active group of elements which transmitted the interrogating pulse, whereby image information representing the position of organ 14 is transmitted to the receiving electronics of the conventional pulse generator/receiver (FIG. 3).

The sector scan produced by the probe 10 is eventually completed by the activation of the leftmost group of transducers of the array 22, which produces beam 34.

In accordance with the present invention, the interior cavity of the probe 10 is filled with a fluid 36 such as a fluorocarbon (i.e. a compound of the general formula $C_nF_{2n+2}$) which has a very low sound propagation velocity. Typically, the sound velocity contemplated for the fluid 36 is on the order of $0.5 \times 10^5$ cm/sec, which is about one-third of the sound velocity of water (the primary component of human tissue). A typical fluorocarbon suitable for this purpose is a dielectric coolant known as Fluorinert FC 72 manufactured by 3M (whose sound velocity at 25° C. is $0.512 \times 10^5$ cm/sec).

It is inherent in the operation of probes of this type that reflections will be produced at the window 28. In a similar manner, there are reflections from the array 22. Multiple reflections produced between these surfaces, e.g. beams that travel from the array to the window, back to the array, then to the window, and back to the array to be detected again, are perceived by the receiving electronics as spurious echoes or artifacts which interfere with the gathering of diagnostic information. These artifacts can be essentially eliminated by making the probe 10 large enough to where the travel time of the ultrasonic beam between the array 22 and the window 28 is slightly greater than the travel time of the beam to the farthest point in the body 12 which needs to be observed. In this manner, the artifacts impinge upon the transducers 22 while they are not in the receiving mode.

Inasmuch as the penetration of the ultrasonic beam for diagnostic purposes needs to be about 20 cm, a water-filled probe 10 would have to have a radius in excess of 20 cm to avoid the above-described reverberation artifact. It will readily be appreciated that a probe of that size would be heavy and clumsy. The use of a slow-velocity fluorocarbon as the probe fluid 36 makes possible a considerable reduction in the size and complexity of probe 10. To begin with, the radius of the probe needs to be only 7-8 cm because it takes the beam as much time to travel that distance in the fluorocarbon fluid as it does to travel the 20 cm distance in the patient's body. Secondly, the refraction caused by the velocity change at the window 28 makes it possible to sweep the beam in the patient's body through an arc of 90° by moving the beam inside the probe 10 through less than 30°.

The slow velocity of the fluid 36 also considerably reduces the beam spread loss which is present in water, and therefore permits a great reduction in the number of total transducer elements. The beam spread loss is determined by the beam spread angle and the distance traveled from the transducer to the window. The beam spread angle is approximately $$A = W/D$$

where W is the wavelength and D is the distance across the active transducer area.

Because the sound velocity in the transducer of this invention is about ⅓ that of water, the wavelength is ⅓ of that in water for the same sound frequency, and hence the beam spread angle is also ⅓ of the angle present in water. Furthermore, the distance from the transducer to the window is also ⅓ of the distance needed in water. Thus, the active area can be reduced to 1/9 of the area needed in a water path transducer. This reduction results in a considerable simplification of the switching electronics required for the scanning of the beam.

Figure 4:
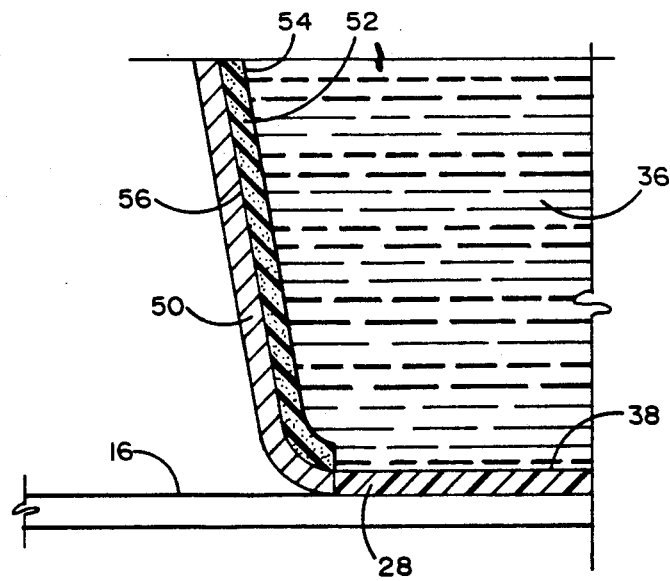
FIG. 4 is an enlarged fragmentary vertical section of the probe of this invention illustrating the window and scatter-absorbing wall lining of this invention.

It is consequently highly desirable to use as slow a fluid as possible in a curved-array probe. However, the use of such a fluid creates certain problems which this invention resolves. Referring to FIG. 4, the window 28 and the adjacent wall portion 50 of the probe 10 are shown in more detail.

When a slow fluid 36 was to be used in a curved-array probe, it was necessary for the window 28 to meet several contradictory requirements. First, the window material had to match the acoustic velocity of skin to avoid reverberations within the window; secondly, it had to be thin to minimize reverberations because an exact match with skin is seldom possible; thirdly, the window had to have a low acoustic velocity to prevent the reflection coefficient from becoming critically high at incidence angles as low as 14°–15° from the vertical; and fourthly, it had to be very stiff to prevent large focal distortions from occurring as a result of minute deflections of the window.

With the acoustic velocity of the slow fluid 36 being about one-third that of human skin, the first and third requirements are mutually exclusive. Likewise, the second and fourth requirements are mutually exclusive because low-velocity materials are inherently soft, and hard materials such as Lucite have an acoustic velocity of $2.5 \times 10^5$ cm/sec or more, which would cause total internal reflection.

In accordance with the invention, the window 28 is made of a polyionomer material with an acoustic velocity between about $1.5 \times 10^5$ cm/sec (the approximate velocity of human skin) and $1.8 \times 10^5$ cm/sec (at which total reflection would occur within the probe 10 before the beam could reach its maximum angle). A match between the acoustic velocities of the skin and the window material is desirable, though not consistently achievable due to differences in skins; however, it is more important for the window material to be as stiff as possible, in order to allow it to be made as thin as possible to minimize internal reverberation and attenuation. A suitable material is a polyionomer marketed by E.I. DuPont de Nemours Co. under the trademark Surlyn. This material has an acoustic velocity of about $1.8 \times 10^5$ cm/sec, and is sufficiently stiff to be essentially nondeformable in clinical use at a window thickness of only about 1.8 mm.

Because of the window's close velocity match with human skin and its tolerable thickness in view of that match, reverberation within the window is held within acceptable limits. However, the high acoustic velocity of the window material does result in strong reflections at the fluid-window interface 38, particularly near the extreme positions 26, 34 of the beam (FIG. 1). Fortunately, the reflection coefficient of the surface 38, although it rapidly increases critically beyond about 15° from the vertical, remains sufficiently near constant below that angle to allow the array 22 to scan, with a reasonably constant signal amplitude, a full 90° sector due to the refraction effect of the slow fluid 36 as explained below.

The direct reflections or reverberations between the window surface 38 and the array 22 are of no concern because, as explained above, they reach the array 22 at a time when it is not in the receiving mode. However, the considerable scatter resulting within the probe 10 from the parameters of the inventive construction presents a significant problem. A related problem arises from the fact that, for both cost and image resolution reasons, the array 22 must be so constructed that the center-to-center spacing of its transducer elements exceeds one wavelength of the ultrasound beam. Consequently, artifact-producing grating lobes of ultrasonic energy are produced on both sides of the beam, and it is essential that these grating lobes be effectively suppressed when they impinge upon the walls of the probe.

In addition to its low-velocity properties, the probe fluid is inherently chosen for its low attenuation. Consequently, artifacts due to reflections of grating lobes and scatter from the probe's side walls 50 (FIG. 4) can only be avoided by making the side walls 50 highly absorptive. In accordance with the invention, this is achieved by coating or lining the side walls 50 with a chemically blown, open-celled polyether urethane foam 52 whose cell diameter at its surface 54 is slightly less than one wavelength (i.e. on the order of 0.14 mm at 3.25 MHz in Fluorinert FC 72).

In the preferred embodiment of the invention, the cell diameter of the material 52 increases slightly in diameter from its surface 54 toward its base 56 at which it is bonded to the wall 50. A suitable foam material for this purpose is the acoustic embossed foam marketed under the trademark E-1-25-E-PSA by E.A.R. division of Cabot Laboratories. This material is uniquely suited for use with Fluorinert, which prevents the formation of undesirable air bubbles during its impregnation when the probe 10 is being filled.

Figure 2:
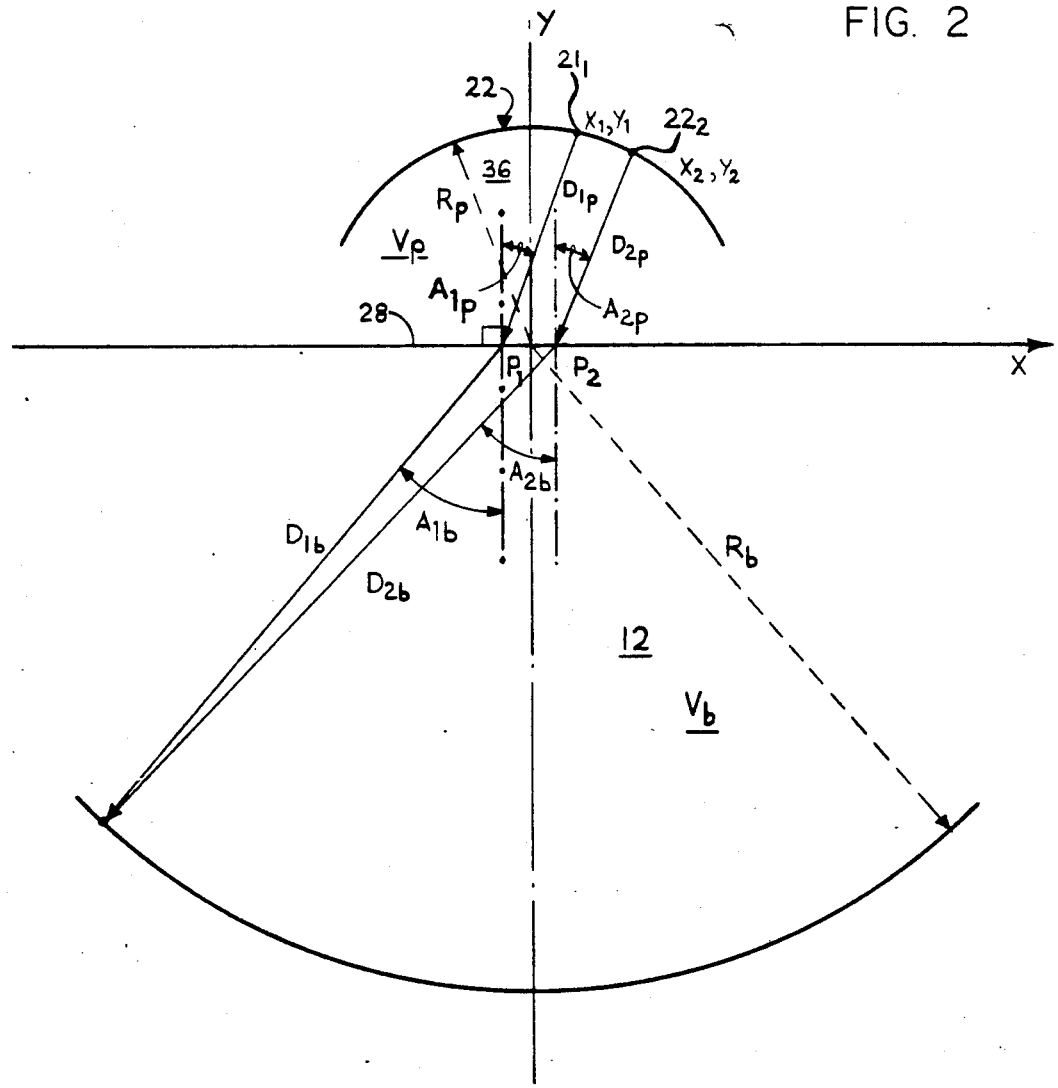
FIG. 2 is a beam geometry diagram showing the relationships which enter into the determination of the pulse delay between the transducer elements.

FIG. 2 illustrates a manner in which the ultrasonic beam can be focused along a desired curve. For the purposes of FIG. 2, it has been assumed that the beam is produced by a group of two elements rather than thirty-two, but the principles involved are equally applicable in both cases.

Let us assume that the curved array 22 of FIG. 2 has a radius $R_p$, and the scanning beam is to be focused along an arc of a circle of radius $R_b$ centered at the center of the window 28. A beam produced by impulses from a pair of transducers $21_1$ and $21_2$ of the array 22, located at points $x_1$, $y_1$ and $x_2$, $y_2$ on the array 22, respectively, will focus at a point $x_f$, $y_f$ in the body 12 if the sound waves from the two transducers arrive at point $x_f$, $y_f$ at the same time. The transit time of the pulse from $x_1$, $y_1$ to $x_f$, $y_f$ is:

$$T_1 = \frac{D_{1p}}{V_p} + \frac{D_{1b}}{V_b} \tag{1}$$

as will be apparent from FIG. 2. In Formula (1), $D_{1p}$ is the distance between the element 21 and the window 28; $D_{1b}$ is the distance between the impact point of $D_{1p}$ at the window 38 and the point $x_f$, $y_f$; $v_p$ is the sound velocity in the probe fluid 36; and $v_b$ is the sound velocity in the body 12. The point P, where the beam intersects the window 28 must satisfy Snell's Law, i.e., $$\frac{\sin A_{1p}}{\sin A_{1b}} = \frac{V_p}{V_b} \tag{2}$$

Likewise, the transit time of the pulse from transducer $x_2$, $y_2$ to point $x_f$, $y_f$ can be expressed as:

$$T_2 = \frac{D_{2p}}{V_p} + \frac{D_{2b}}{V_b} \tag{3}$$

In order for the beam produced by transducers $x_1$, $y_1$ and $x_2$, $y_2$ to focus at $x_f$, $y_f$, it is necessary that:

$$t = T_2 - T_1 \tag{4}$$

in which t is the delay between the pulsing of element $x_2$, $y_2$ and the subsequent pulsing of element $x_1$, $y_1$.

Knowing the relative positions of the transducer elements 21 in the array 22 of FIG. 1, it is thus possible, by the application of conventional geometry, to calculate the precise delays necessary for the focusing of the scan. Suffice it to say that the pulsing delays necessary to accomplish the above-described focusing in the preferred embodiment of this invention are on the order of 1 μs, which is substantially less than the delays on the order of 10 μs which would be necessary if the scan were produced by a phased linear array of transducers placed directly against the skin.

Because the implementation of accurate delays is one of the more difficult design problems associated with ultrasonic arrays, and because the delay error is generally proportional to the delay, this reduction can significantly reduce delay error. Delay error is one of the more significant factors limiting the quality of images produced by arrays. In addition, the 10 μs accuracy of the delay elements required in this type of application represents a standard off-the-shelf 1% accuracy in a 1 μs element, as compared to an expensive 0.1% accuracy in a 10 μs element.

FIG. 3 illustrates the manner in which focusing is accomplished. A pulse generator/receiver 32 produces short pulses of 3.5 MHz energy at a repetition rate of 3.84 kHz. Between the pulses, the pulse generator/receiver 32 is switched to the receive mode in a conventional manner in order to listen for echoes. The pulses produced by the generator 32, as well as the signals received by the active group of the tranducer elements of the array 22, are delayed varying amounts of time through a series of delay lines 40. The individual delays of delay lines 40 can be variable under the control of a computer 42 to follow the scanning sequence established by the scan sequencer 46.

The individual transducers 21 making up the active group of array 22 are selected just prior to each pulse by a switching matrix 44 controlled by the sequencer 46. The computer 42 can be programmed in a conventional manner to calculate and adjust the delay associated with any given active transducer element in accordance with the geometry of the probe and the position of each transducer element 21 with respect to the adjacent element, as detailed in the foregoing description of FIG. 2.

It will be seen that the present invention provides a small, simple, inexpensive yet accurate probe for medical ultrasonic diagnostic apparatus by combining the advantages of a curved transducer-array with those of a low-velocity probe fluid. The teachings of the invention can be carried out in a number of ways, as those skilled in the art will appreciate, and the invention therefore should not be construed as limited except by the scope of the following claims.

We claim:

1. An ultrasonic probe for medical diagnostic apparatus, comprising:
   (a) a housing;
   (b) a relatively thin, acoustically transparent window formed in said housing for application to a patient's skin, said window being formed of a material essentially non-deformable by said application of said window to said patients's skin having an acoustic velocity approximating that of human skin, and being sufficiently thin to substantially suppress reverberations within said window;
   (c) a curved array of transducer elements disposed in said housing opposite said window;
   (d) means for activating said elements in successive groups so as to produce a sector scan through said window, said fluid having a sound propagation velocity substantially slower than that of water.

2. The probe of claim 1, in which said housing includes side wall means internally coated with an ultrasound absorption material of sufficient absorbency to absorb grating lobes.

3. The probe of claim 1, in which said window is formed of a single layer of material having a thickness on the order of 1.8 mm when a coupling fluid having an acoustic velocity on the order of $0.5 \times 10^5$ cm/sec is used.

4. The probe of claim 1, in which said window is generally flat.

5. The probe of claim 4, in which the acoustic velocity of said material lies generally within the range of $1.5 \times 10^5$ cm/sec to $1.8 \times 10^5$ cm/sec.

6. An ultrasonic probe for medical diagnostic apparatus, comprising:
   (a) a housing;
   (b) an acoustically transparent window formed in said housing for application to a patient's skin;
   (c) a curved array of transducer elements disposed in said housing opposite said window;
   (d) means for activating said elements in successive groups so as to produce a sector scan through said window, said sector scan being focused outwardly of said housing; and
   (e) fluid means in said housing between said array and said window, said fluid having a sound propagation velocity substantially slower than that of water;
   (f) said window being formed of a polyionomer material essentially nondeformable by said application of said window to said patient's skin and having an acoustic velocity approximating that of human skin.

7. An ultrasonic probe for medical diagnostic apparatus, comprising:
   (a) a housing
   (b) an acoustically transparent window formed in said housing for application to a patient's skin;
   (c) a curved array of transducer elements disposed in said housing opposite said window;
   (d) means for activating said elements in successive groups so as to produce a sector scan through said window, said sector scan being focused outwardly of said housing; and
   (e) fluid means in said housing between said array and said window, said fluid having a sound propagation velocity substantially slower than that of water;
   (f) said housing including side wall means internally coated with an open-celled foam material, the surface cell diameter of said foam material being slightly smaller than one wavelength of said ultrasound in said fluid.

8. The probe of claim 7, in which said material is a polyether urethane foam.

9. The probe of claim 8, in which the cell diameter of said foam material increases in the direction from its surface to its base.

* * * * *